US005532493A

United States Patent [19]
Hale et al.

[11] Patent Number: 5,532,493
[45] Date of Patent: Jul. 2, 1996

[54] OPTICAL WAVEGUIDE CHEMICAL AND BIOLOGICAL SENSOR

[75] Inventors: Zoë M. Hale, Monument, Colo.; Robert Marks, Cambridge, England

[73] Assignee: The United States of America as represented by the Secretary of the Air Force, Washington, D.C.

[21] Appl. No.: 319,710

[22] Filed: Oct. 7, 1994

[30]     Foreign Application Priority Data

Jan. 21, 1994 [GB]  United Kingdom ............... 9401170

[51] Int. Cl.⁶ ........................ G01N 21/64; G02B 6/16
[52] U.S. Cl. .................. 250/458.1; 385/12; 385/123
[58] Field of Search ..................... 250/361 C, 458.1, 250/459.1; 385/123, 12

[56]            References Cited

U.S. PATENT DOCUMENTS 4,981,338  1/1991  Bobb et al. ...................... 385/12

FOREIGN PATENT DOCUMENTS

| 3128120 | 6/1983 | Germany | 385/123 |
| 4304545 | 8/1994 | Germany | 385/12 |
| 57-62004 | 4/1982 | Japan | 385/12 |
| 177503 | 10/1994 | Japan | 385/123 |

*Primary Examiner*—Carolyn E. Fields
*Attorney, Agent, or Firm*—Bobby D. Scearce; Thomas L. Kundert

[57]            ABSTRACT

An optical waveguide sensor particularly useful as a chemical or biological sensor is described which comprises a single mode fibre optic waveguide including a core surrounded by a cladding and having a tapered portion which tapers adiabatically inwardly to a waist of diameter typically about that of the original core, and then adiabatically outwardly by variation of the cladding whereby under operating conditions the evanescent electromagnetic field associated with the guided mode of the waveguide is externally accessible in the region of the tapered portion; an optical source, such as a laser, optically coupled to one end of the waveguide; and a detector coupled to the other end of the waveguide for detecting optical radiation modulated or coupled into the waveguide at the tapered portion. The tapered portion is preferably in the form of a loop to facilitate construction of the sensor as a probe, and includes a binder for binding a chemical or biological compound, for example, a silane for use in conjunction with a recognition entity.

10 Claims, 4 Drawing Sheets

OPTICAL WAVEGUIDE CHEMICAL AND BIOLOGICAL SENSOR

RIGHTS OF THE GOVERNMENT

The invention described herein may be manufactured and used by or for the Government of the United States for all governmental purposes without the payment of any royalty.

BACKGROUND OF THE INVENTION

The invention relates to an optical waveguide sensor, for example, for use as a chemical or biological sensor.

The evanescent wave portion of an electromagnetic field propagating through an optical waveguide characteristically penetrates up to several hundred nanometers into the medium surrounding the optical waveguide. This evanescent wave can excite fluorescent molecules, e.g., fluorophores, to fluoresce when these molecules are near the optical waveguide surface, within the depth of penetration. The application of this phenomenon to an immunoassay sensor, wherein the biological recognition (binding) of antigen to antibodies attached to the waveguide surface with the concomitant displacement of fluorescent-labelled antigen is measured as a change in fluorescence, was first disclosed in "A New Immunoassay Based on Fluorescence Excitation by Internal Reflection Spectroscopy" by Kronick and Little, Journal of Immunological Methods 1975, Vol. 8, page 235.

The use of optical fibres as a special class of waveguides for immunoassay sensors is also known. For example, U.S. Pat. No. 4,447,546 discloses the use of optical fibers as waveguides which capture and conduct fluorescence radiation emitted by molecules near their surfaces.

U.S. Pat. No. 5,061,857 describes an optical sensor in which the end of a multimode optical fiber is tapered. The evanescent field excites fluorescence which is coupled back into the optical fiber and returns to a detector. The problem with this approach is that the detector is relatively inefficient in capturing the fluorescence.

SUMMARY OF THE INVENTION

In accordance with one aspect of the present invention, an optical sensor comprises a single mode fiber optic waveguide including a core surrounded by a cladding and having a tapered portion which tapers adiabatically inwardly to a waist and then adiabatically outwardly by variation of the cladding whereby under operating conditions the evanescent electromagnetic field associated with the guided mode of the waveguide is externally accessible in the region of the tapered portion; an optical source optically coupled to one end of the waveguide; and a detector coupled to the other end of the waveguide for detecting optical radiation modulated or coupled into the waveguide at the tapered portion.

We have devised a new type of optical sensor which enables optical radiation modulated or generated in the region of the tapered portion, for example fluorescence excited by the evanescent field, to be efficiently coupled into the waveguide while the initial guided optical field (fundamental mode) itself suffers a substantially low transmission loss. Typically, the transmission loss through the optical fiber, including the tapered region, will be no more than 0.1 dB.

The radiation coupled into the waveguide will typically comprise fluorescence but could include chemiluminescence or other radiation.

The waist typically has a diameter of the order of the original fiber core diameter.

In some cases, the tapered portion can have a linear form but preferably the tapered portion is in the form of a loop. This is particularly advantageous since it enables the sensor to be constructed in the form of a probe which in some cases could be inserted into a sample of volume one milliliter or less, for example physiological fluids of a human or animal, to enable materials to be sensed in situ. It also allows particularly robust mounting arrangements to be achieved. For example, in a preferred arrangement, the sensor further comprises a mount supporting the tapered optical fiber. Typically, in the case of a loop, the mount may include a removable cap for positioning over the loop.

Typically, the optical source will comprise a laser, for example, an argon ion laser or semi-conductor laser while the detector typically comprises a photodiode. Preferably, a filter is positioned between the optical waveguide and the detector for filtering out optical wavelengths corresponding to those generated by the source. This is particularly important where fluorescence is being sensed which will be at a different wavelength from that of the source. Alternatively, a configuration comprising a fiber element with a tapered region (as described), and a coupler with a known ratio (e.g. 95:5) can monitor the input wavelength via an optical detector to serve as a differential reference.

As mentioned above, a particularly important application of this invention is in the field of chemical and biological sensors. In general, the sensor will not be affected by optical radiation such as fluorescence from molecules spaced from the waveguide (i.e. background interference). Preferably, therefore, the sensor further includes means for binding a chemical or biological compound to the tapered portion of the fiber and for example may comprise a silane for use in conjunction with a recognition entity.

In accordance with a second aspect of the invention, a method of using a chemical or biological sensor in accordance with the first aspect of the invention, the sensor including means for binding a chemical or biological compound provided on the tapered portion comprises placing the tapered portion of the sensor in contact with a sample to be tested whereby a chemical or biological compound to be sensed and corresponding to the binding means on the tapered portion will bind to the tapered portion.

Preferably, the method further comprises treating the tapered portion, after contacting the sample, with a fluorescent indicator which binds to the bound chemical or biological compound; passing optical radiation along the waveguide whereby the evanescent field in the tapered portion excites fluorescence in the fluorescent system or indicator, the fluorescent energy being coupled into the guided mode of the waveguide; and detecting the presence of the fluorescent radiation.

This method not only allows the presence or absence of the fluorescent indicator to be detected but also enables quantitative measurements to be made.

In the context of the specification, the reference to "optical radiation" includes not only radiation in the visible wavelength but also ultraviolet and infrared radiation and indeed any wavelengths which can be transmitted by optical waveguides.

BRIEF DESCRIPTION OF THE DRAWINGS

Some examples of sensors according to the invention and their methods of construction will now be described with reference to the accompanying drawings.

DETAILED DESCRIPTION OF THE INVENTION

Figure 1A:
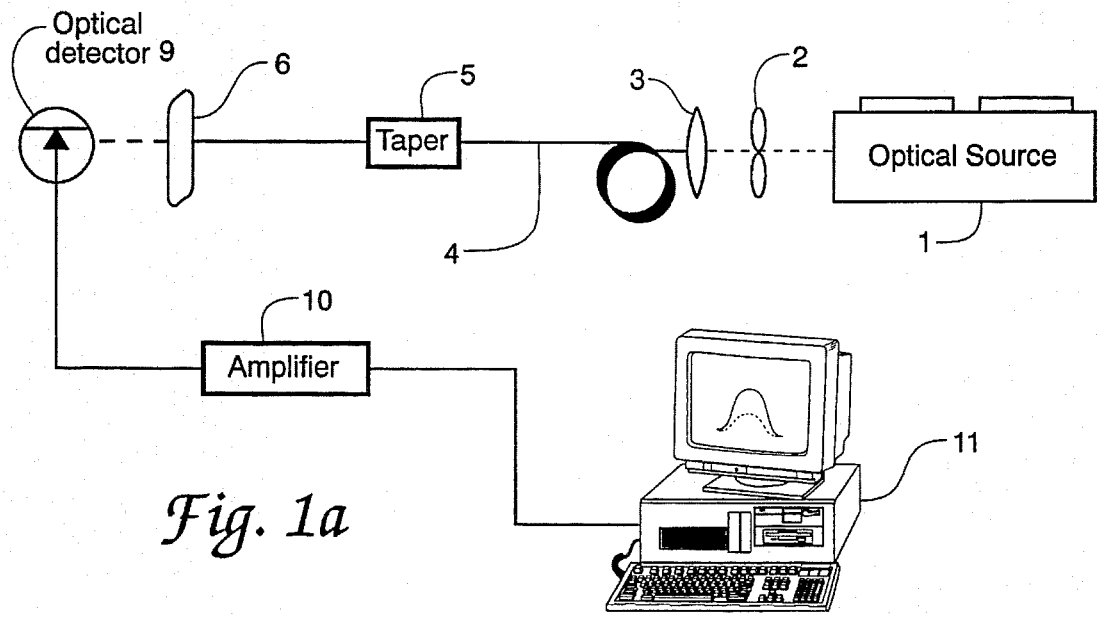
FIGS. 1a and 1b are schematic block diagrams of two examples of a sensor assembly.
Figure 6:
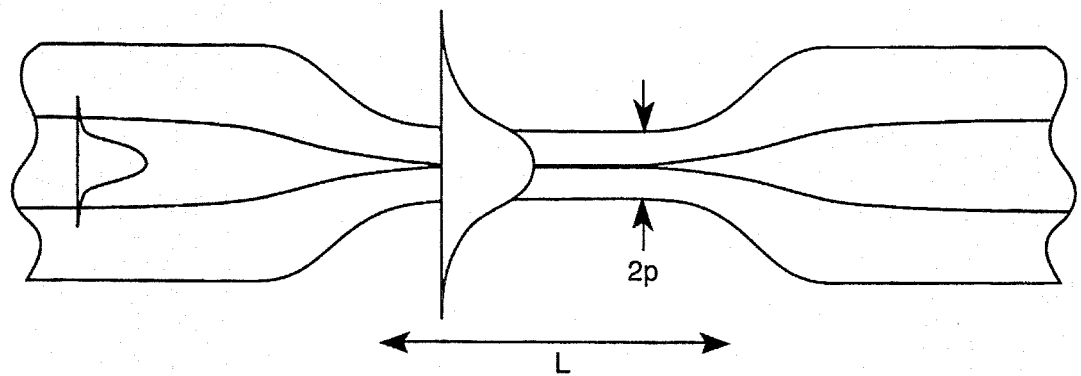
FIG. 6 portrays notation used in the mathematical analysis.

FIG. 1a illustrates a typical sensing assembly comprising an optical source 1 which generates a laser beam centered at a wavelength of 488 nm which passes through an optical chopper 2 and lens 3 into a single mode optical fiber 4. The optical fiber 4 has a biconical tapered portion 5, to be described in more detail below, which is sited in use in the region to be investigated. The taper profile, as illustrated in FIG. 6, has a central waist region of length L and uniform radius $r_o$, with exponential transition from the full radius $R_o$ given by $a(z)=R_o \exp(-z/L)$. In one example, the optical fiber 4 has a numerical aperture of 0.18 and a cut off wavelength of 450 nm. The diameter of the nominally circular core is 1.7 microns with an outer fiber diameter of 80 microns, and a cladding refractive index of 1.458.

As will be explained below, in the tapered portion 5, a high power evanescent field is generated which excites fluorescence in the surrounding region, the fluorescent emissions being coupled back into the fundamental guided mode of the fiber. These fluorescent emissions together with residual power from the input optical source 1 pass along the optical fiber 4 to a lens 6 and optical filter for fluorescent radiation above 515 nm which filters out completely the input optical radiation at 488 nm. The filtered radiation impinges upon a photodetector 9 which generates an output signal which is fed via a lock-in amplifier 10 to a microprocessor 11.

Figure 1B:
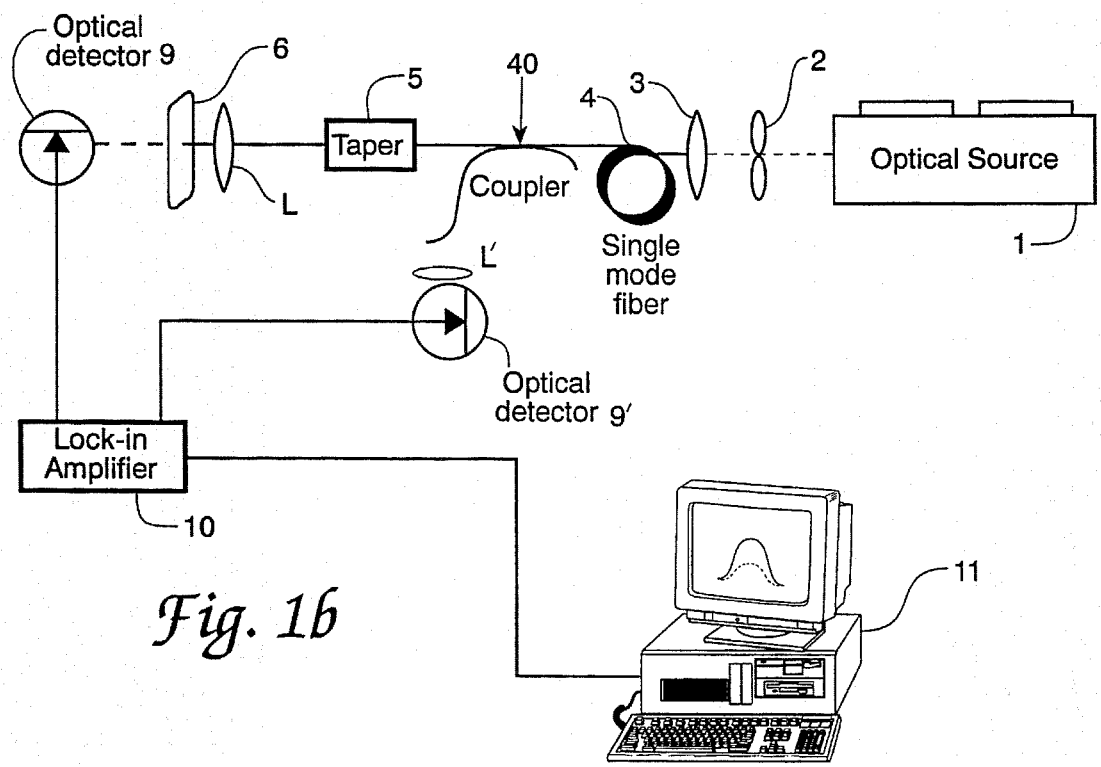

FIG. 1b illustrates a modification of the FIG. 1a example in which an optical coupler 40 is connected to the optical fibre 4. The coupler has a ratio of for example 95:5 and monitors the input wavelength from the optical source 1. The portion of the signal removed by the coupler 40 is fed to an auxiliary optical detector 9' via a lens L', the output of the optical detector 9' being fed to the lock-in amplifier 10 so as to serve as a differential reference.

Figure 2:
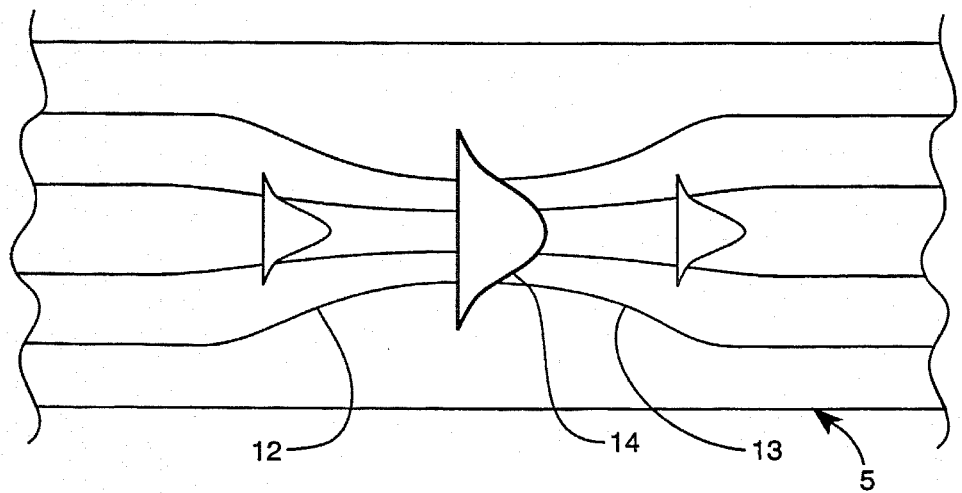
FIG. 2 illustrates a tapered portion of an optical fiber.

FIG. 2 illustrates the tapered portion 5 in more detail where it can be seen that the tapered portion comprises a pair of generally conically tapered sections 12, 13 each tapering towards a waist 14. The waist diameter can vary between 0.5 microns and 10 microns, preferably between 0.5 and 1.5 microns, while the overall length of the tapered portion is preferably at least 5 mm.

The tapered section can be manufactured in a variety of ways which are known in the art. The main requirement is to achieve an adiabatically-tapered portion so as to minimize power losses and maximize the evanescent field in the region of the tapered portion. A typical example of known methods for constructing optical fiber tapers is described in Electronics Letters 29 August 1991, vol. 27 no. 18, pages 1654–1656.

As the fiber is being tapered, the changing radius may cause coupling of the optical energy in the guided mode of the single mode optical fiber ($LP_{01}$ mode) to higher order ($Lp_{lm}$) modes. Such coupling would be undesirable since the higher order modes will not be recaptured back into the core, resulting in a taper with (wavelength dependent) transmission loss. If the taper is formed without coupling into these higher order modes, all the input light will be recaptured, at the far end of the taper, into the core. Such a tapered single mode optical fiber with negligible loss can be termed adiabatic. The best method of minimizing loss is to use the Love criterion for an adiabatic taper profile:

$$\frac{dr}{dz} < \frac{r}{z\beta}$$

where $$z\beta = \frac{2r_0}{\beta_{01} - \beta_{02}}$$

is the beat length between $LP_{01}$ and the next highest $Lp_{lm}$ modes, $\beta$ is the propagation constant for the mode and r is the radius of the taper. The slope of the taper should always be much smaller than the normalized inverse beat length $r/z\beta$. From J D Love "Application of a low-loss criterion to optical waveguides and devices", IEE Proceedings Part J, Volume 136, Number 4, August 1989, pp 225–8.

Figure 3:
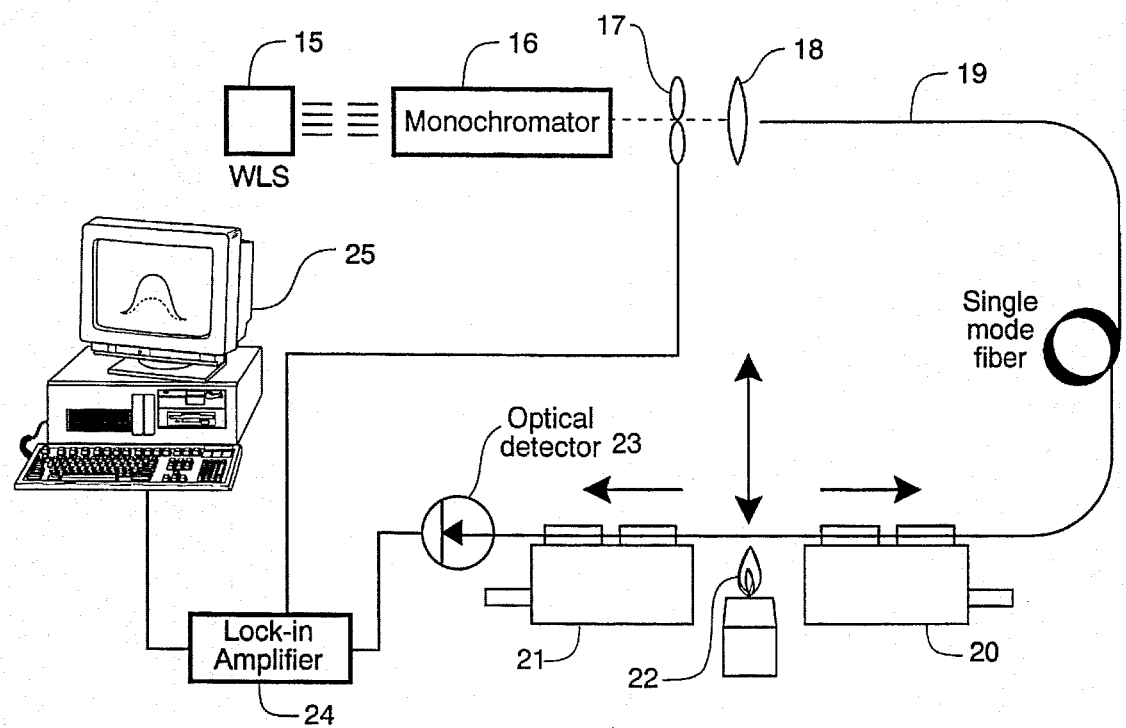
FIG. 3 is a schematic diagram of apparatus for manufacturing the tapered portion.

An example of apparatus for manufacturing a tapered portion is shown in FIG. 3. In this example, a light source such as a white light source (e.g., halogen lamp) injects light through a monochromator 16 to an optical chopper 17 and a lens 18 into a single mode optical fiber 19. The fiber 19 is held under tension by a pair of motor-driven mounts 20, 21 between which is a flame (the flame may be oxygenated natural gas, oxybutane, oxypropane, or indeed any suitable heat source) 22. The distal end of the fiber 19 is connected to a lock-in amplifier 24 through a photodiode 23; electronic data is then passed to a microprocessor 25. The amplifier 24 is referenced to the optical chopper 17. In operation, the portion of the optical fibre 19 between the mounts 20, 21 is heated by the flame 22 to the softening point of the silica glass and the optical fiber is pulled in opposite directions by the mounts 20, 21 moving outward. While the fiber 19 is being stretched, the power transmitted through it is monitored via the photodiode 23. An acceptable taper has low loss, of the order of 0.1 dB, which is typically achieved in a slow process. The resultant taper is adiabatic: that is, the diameter changes slowly along the length of the taper. Because of this, the fundamental fiber mode that enters the tapered region does not couple appreciably either to cladding or radiation modes. Power guided by the fundamental mode is concentrated in a very small circular cross-section at the taper waist with a diameter of for example about 5 microns. A very small power, of the order of milliwatts, can cause a high power density of kw/cm$^2$, as in E.-G. Neumann Single-Mode Fibers: Fundamentals, Springer-Verlag, Berlin, 1988, page 86.

At the taper waist the fiber core is so small that it plays no role in guiding the light. Guiding is achieved by a new effective waveguide consisting of the fiber cladding and the surrounding medium. The local value of the V number is reduced in proportion to the fiber diameter and in very small diameter tapers (of the order of microns), the fundamental mode field extends into the medium surrounding the cladding. The level of interaction with field, as well as the fluorescent indicator used, determines the efficiency with which the fluorescence can be re-captured into the fiber. The V number is defined as:

$$V = \frac{2\pi\rho}{\lambda} \sqrt{n_1^2 - n_2^2}$$

where $\rho$ is the core radius, $n_1$ is the refractive index of the core, $n_2$ is the refractive index of the cladding, and $\lambda$ is the free space wavelength of light propagating in the fiber.

Figure 4A:
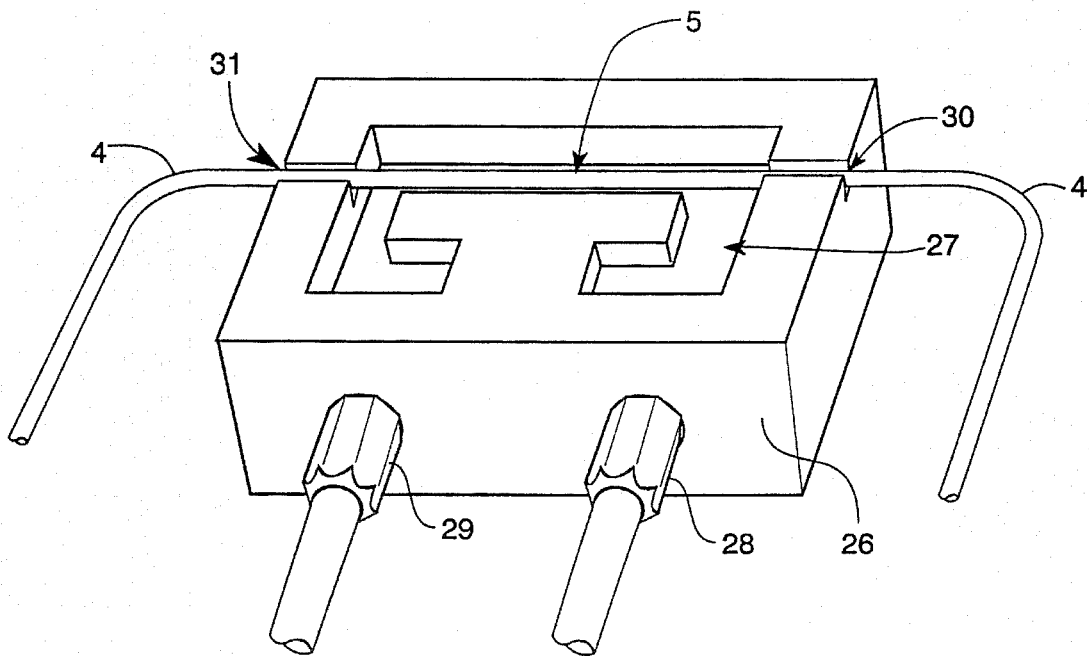
FIGS. 4a and 4b illustrate examples of optical fiber mounts.

In one application, the tapered portion 5 is held in a linear geometry in a mount 26 (FIG. 4a) having a C-shaped channel 27 through which a solution is passed via entry and exit ports 28, 29. The optical fiber 4 is laid through the channel 27 while being supported in laterally spaced grooves 30, 31 and is glued in place. The mount 26 is covered with a cover (PERSPEX™ or any other material; not shown) to close the channel 27 and to prevent contamination of the fiber 4.

Figure 4B:
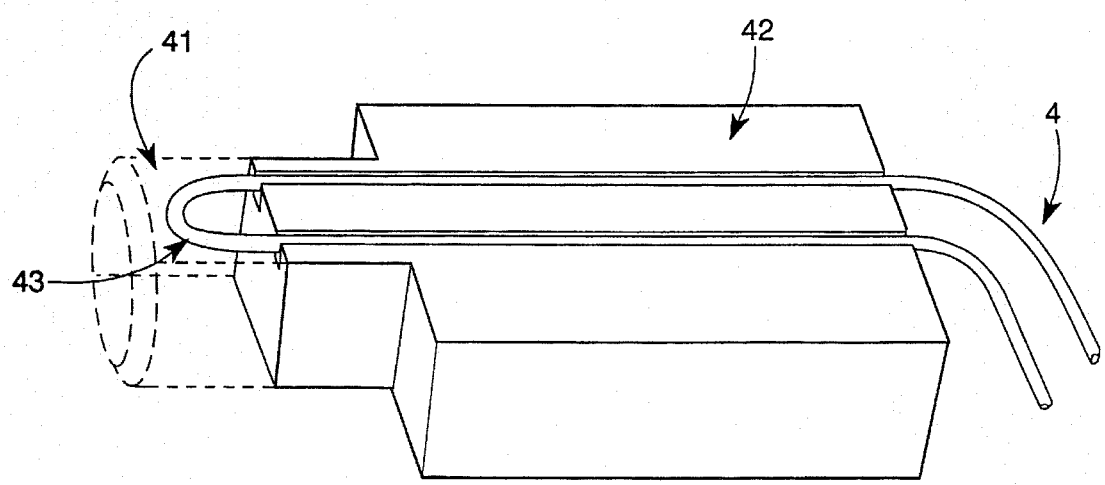
Figure 5:
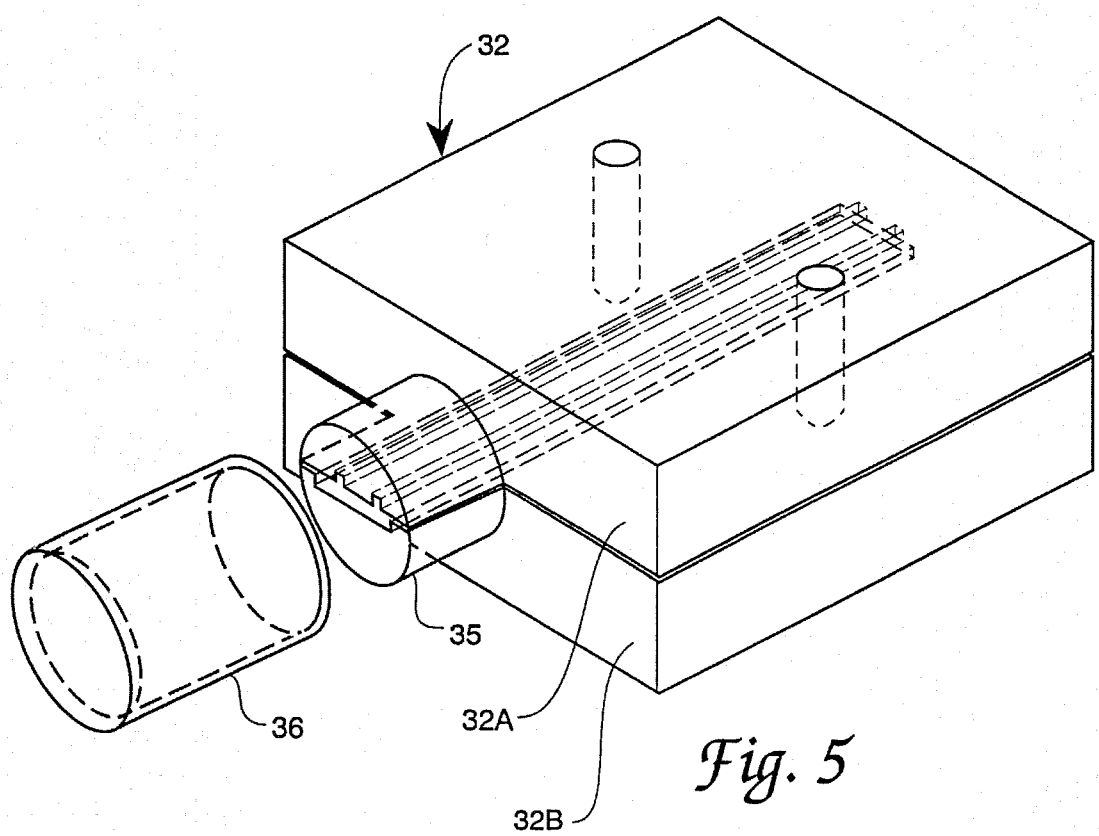
FIG. 5 illustrates details of the optical fiber mount in FIG. 4b.

An alternative mounting arrangement is shown in FIGS. 4b and 5. In this case, a probe is provided defined by a mount 32 comprising upper and lower sections 32A, 32B fastened together by a pair of pins (not shown). The optical fiber 4 extends through a pair of parallel slots 33, 34 extending through the mount 32 and a tongue portion 35. The tapered portion is formed into a loop 5' shown in FIG. 5 which protrudes beyond the edge of the tongue portion 35. A cap 36 is provided which is press fitted over the tongue 35 so that the loop 5' is contained within the cap which, as will be explained below, is filled with the solution to be tested. In the split view of the alternate mounting arrangement presented in FIG. 4b, the optical fiber 4 passes through the mount 42 (brass, stainless steel or other appropriate material) to the apex of the taper loop 43, which is protected by a PERSPEX™ or glass cap 41.

It will be noted that in the examples shown in FIGS. 4b and 5, the solution to be tested is brought to the fiber, however, it is envisioned that the probe could be fabricated based on the principle of using a loop as shown in FIG. 5 and this probe could be inserted directly into the sample, for example a physiological fluid sample from a human or animal body.

As explained above, the primary application of the sensor is as a chemical or biological sensor for sensing fluorescence in a region of the tapered portion. In particular, the sensor will find important application as an immunosensor. In order to sense biological material, such as antibodies or enzymes, a reciprocal recognition molecule must be bound to the optical fiber. It is known that certain compounds are suitable for achieving this, for example silanes. Subsequent compounds can be in turn bound to the silane.

In this example, we shall describe how the presence of cholera toxin antibodies can be sensed. The tapered portion of the optical fiber is initially treated with a suitable binding agent, in this case 3-Glycidoxyproypyltrimethoxysilane. This may be achieved, in the case of the FIG. 5 arrangement by filling the cap 36 with the silane, mounting the cap on the mount 32, and then incubating at 50 degrees Celsius (though other temperatures to 100 degrees Celsius could be used).

The treated optical fibre is then treated with 11.6 mM HCL at not less than 50 degrees Celsius, then with $NaIO_4$ which converts the silane glycidyl moiety to an aldehyde. After binding a protein recognition molecule to the aldehyde, a Schiff's base is formed which is reduced by treating with a reducing agent (for example, sodium cyanoborohydride). The optical fiber loop having the bound cholera toxin B subunit or cholera toxin B subunit derived synthetic peptide ($CTP_3$) is then placed in the sample to be tested. Finally, the loop is exposed to a solution which contains fluorescent molecules which bind to the antibody, if present. Light is then passed along the optical fiber so that a high power evanescent wave is generated around the tapered portion of the optical fibre and this excites the fluorescent molecules which are attached. Fluorescence is then coupled into the optical fiber and passes to the photodetector where it is detected. The presence of fluorescence then indicates the presence of the cholera toxin antibodies.

In some cases, the probe arrangement shown in FIG. 5 could be disposable but in other arrangements following a test process, tapered portion of the optical fibre could be reused after appropriate treatment, for example, with a chaotropic buffer.

In the Appendix, we explain in more detail why the external fluorescence in a dye solution surrounding the tapered portion of the fiber is coupled into the fundamental mode of the tapered single mode fiber.

APPENDIX

The analysis is based on Snyder and Love "Optical Waveguide Theory", Chapman & Hall, London, England, 1983, who have given a general account of radiative capture into the core of an optical fiber. For simplicity, we assume that the taper waist is of constant radius p and length L (see FIG. 6). At the taper waist, the original core of the fiber is so small that it can be neglected, so that the light is guided by a new effective waveguide consisting of the fiber cladding and external medium. At the taper waist the pump light excites the dye molecules into the first excited state, from which they fluoresce as an incoherent mixture of radiative dipoles. A dipole at position $\vec{r}_d$ can be represented by a current density $\vec{J}$ given by:

$$\vec{J} = \vec{\alpha}\delta^3(\vec{r} - \vec{r}_d) \quad (2)$$

where $\delta$ is the Dirac-delta function.

The vector $\vec{\alpha}$ describes the strength and direction of the dipole, and depends on the detailed dipole moment of the dye molecule. For our purposes we will assume that all the molecules radiate incoherently and isotropically, then the following ensemble average will apply:

$$\langle \alpha_i \alpha_j \rangle = \delta_{ij} \frac{\langle \alpha^2 \rangle}{3} \quad (3)$$

Equation 3 is derived at the end of this Appendix.

To calculate the fluorescence coupled into the fundamental mode of the taper, we need to know the amplitude of the mode excited by the current source in equation (2). This is given by Snyder and Love as:

$$\alpha_\nu = \frac{1}{4N} \int (\vec{e}_\nu)^e \cdot \vec{J} e^{-i\beta \zeta} dV \quad (4)$$

where $\nu$ refers to either of the two orthogonal polarizations of the fundamental modal field $e_\nu$, with propagation constant $\beta$ and normalization N defined so that the power carried by the mode is:

$$P_\nu = |a_\nu|^2 N \quad (5)$$

and where the normalization of the modal field is defined so that:

$$\int_0^{2\pi}\int_0^\infty e_\nu^2\, r\, dr\, d\phi = 1, N = \frac{n_1}{2}\sqrt{\frac{\epsilon_o}{\mu_o}} \quad (6)$$

The integral in equation (6) is over the entire transverse cross section, and $n_1$ is the refractive index of the taper (normally silica). Combining equations (2) through (6), and summing over the two polarizations v=x,y, we find that the average power in the fundamental mode excited by a fluorescing dye molecule at radius $r_d$ is given by:

$$P = \frac{1}{16N} \frac{2}{3} \langle \vec{\alpha}^2 \rangle |\vec{e}_o(r_d)|^2 \tag{7}$$

In equation (7) we have neglected the z component of the field; we have also dropped the polarization subscript since the fundamental mode has the same radial form $e_o$ for the x and y polarization. We now combine equation (7) with the distribution $n_d(r_d)$ of dipoles at radius $r_d$ excited by the fundamental pump mode in the taper. This will be expressed in terms of the following parameters:

$n_e$ concentration of the dye molecules
$\sigma_a$ absorption cross section of the dye molecule
$\xi$ fluorescent lifetime of the dye molecule
$\phi$ quantum efficiency of the dye The density distribution of radiating dye molecules at radius $r_d$ is then given by:

$$n_d(r_d) = \gamma \cdot |\vec{e}_p(r_d)|^2 \tag{8}$$

where $$\gamma = \frac{n_c \tau_f \sigma_a \lambda P_{inc}}{hc}.$$

The incident pump power is $P_{inc}$ and the modal field of the pump is $\vec{e}_p$; h is Planck's constant, c is the speed of light and $\lambda$ is the wavelength of the radiation. Equation 8 comes about because the photon flux is $P_{inc}$/photon energy, which is $$\frac{P_{inc}\lambda}{hc}.$$

To obtain the flux per unit area at radius $r_d$ this must be multiplied by $|\vec{e}_p(r_d)|^2$. Each dye molecule has an absorption cross section $\sigma_a$ and a concentration $n_c$, so that the excitation rate per unit volume of the dye is $$\frac{n_c \sigma_a P_{inc}\lambda}{hc} |e_p(r_d)|^2.$$

The rate of decay from fluorescence is 1/τf, which leads to equation (8) for the steady state concentration of excited dye molecules. Multiplying equations (7) and (8), and integrating over all molecules we obtain the following expression for the total fluorescent power captured into the fundamental mode of a taper of length L:

$$P_{cap} = \frac{L\gamma\phi}{16N} \frac{2}{3} \langle \vec{\alpha}^2 \rangle \int_0^{2\pi} \int_{r=\rho}^{\infty} |\vec{e}_o(r)|^2 |\vec{e}_p(r)|^2 \, r \, dr \, d\phi \tag{9}$$

The integral in equation (9) is over the region surrounding the taper, with a radius of $\rho$ (see FIG. 4). We have also dropped the subscript on $r_d$ since it is being integrated over. In order to estimate the efficiency of fluorescent capture we now need the total power radiated by all the dye molecules. The power radiated by one molecule is given by Snyder and Love as:

$$P_{rad} = \langle \vec{\alpha}^2 \rangle \frac{k_o^2 n_2}{12\pi} \sqrt{\frac{\mu_o}{\epsilon_o}} \tag{10}$$

where $$k_o = \frac{2\pi}{\lambda}$$

and $n_2$ is the refractive index of the surrounding dye solution. We can neglect the effect of the presence of the fiber on the total radiation. The total fluorescent power is given by combining equation (10) with the density of dye molecules, given by equation (8). We then obtain:

$$P_{tot} = \frac{L\gamma\phi}{12\pi} \langle \vec{\alpha}^2 \rangle k_o^2 n_2 \sqrt{\frac{\mu_o}{\epsilon_o}} \int_0^{2\pi} \int_{r=\rho}^{\infty} |\vec{e}_p|^2 \, r \, dr \, d\phi \tag{11}$$

We define the efficiency of fluorescent capture as the ratio $$\eta = \frac{P_{cap}}{P_{tot}}.$$

From equations (9) and (11) this is given by:

$$\eta = \frac{\pi}{k_o^2 n_1^2} \frac{\int_0^{2\pi} \int_{r=\rho}^{\infty} |\vec{e}_o|^2 |\vec{e}_p|^2 \, r \, dr \, d\phi}{\int_0^{2\pi} \int_{r=\rho}^{\infty} |\vec{e}_p|^2 \, r \, dr \, d\phi} \tag{12}$$

In our experiment, the refractive index of the dye solution was close to that of the silica taper, so that we may put $n_1 \approx n_2$. In addition, the pump and fluorescence wavelengths are normally close enough so that we may approximate the modal fields $\vec{e}_p$ and $\vec{e}_o$. This allows equation (12) to be written in a slightly simpler form:

$$\eta = \frac{\pi}{k_o^2 n_1^2} \frac{\int_0^{2\pi} \int_{r=\rho}^{\infty} |\vec{e}_o|^4 \, r \, dr \, d\phi}{\int_0^{2\pi} \int_{r=\rho}^{\infty} |\vec{e}_o|^2 \, r \, dr \, d\phi} \tag{13}$$

In both equations (12) and (13) the integrals are over the region external to the taper radius $\rho$. Equation (13) can be evaluated analytically by using the Gaussian approximation [14] for the fundamental mode of a waveguide with radius $\rho$:

$$e_o(r) = \frac{1}{\sqrt{\pi r_o^2}} e^{-r^2/2r_o^2} \tag{14}$$

where $$r_o = \frac{\rho}{\sqrt{2\log_e V}}$$

and V is defined in equation (1). The Gaussian approximation holds true vor V>1. The integral in equation (13) can now be easily evaluted to give this expression for the efficiency:

$$\eta = \frac{1}{(k_o \rho n_1)^2} \frac{\log_e V}{V^2} \tag{15}$$

Writing equation (15) using the definition of V from equation (1), we arrive at the final expression for the efficiency:

$$\eta = \frac{\log_e V}{V^4} \frac{(NA)^2}{n_1^2} \quad (16)$$

NA, the numerical aperture of the taper, is given by $(n_1^2 - n_2^2)^{1/2}$. In this form $\eta$ can easily be seen to be always less than one. The smallest tapers used in our experiments had diameters of approximately 0.5 microns. The external dye index was adjusted to 1.44, which, combined with the index of refraction for the cladding of 1.458, corresponded to an NA of 0.23. The fluorescent wavelength was 0.526 microns, yielding an estimated efficiency of 0.2%. For tapers with a 2 micron diameter the corresponding efficiency would be about 0.04%. Results using multimode polished fibers gives efficiencies of approximately $10^{-4}$.

The derivation of equation (3) is a follows. The Cartesian components of $\vec{\alpha}$ can be expressed in polar form as $\alpha_x = \alpha \sin\theta \cos\phi$ $\alpha_y = \alpha \sin\theta \sin\phi$ $\alpha_z = \alpha \cos\theta$ We assume that the direction of $\vec{\alpha}$ is distributed isotropically in space. This means that its direction is described by the probability distribution $P(\theta,\phi)$:

$$P(\theta,\phi) = \frac{\sin\theta}{4\pi} \text{ where } \int_0^\pi d\theta \int_0^{2\pi} d\phi P(\theta,\phi) = 1.$$

The average $\langle \alpha_i \alpha_j \rangle$ is defined by:

$$\langle \alpha_i \alpha_j \rangle = \int_0^\pi \int_0^{2\pi} \alpha_i \alpha_j P(\theta,\phi) d\theta d\phi$$

and a little algebra gives the following:

$$\langle \alpha_x \alpha_y \rangle = \langle \alpha_x \alpha_z \rangle = \langle \alpha_y \alpha_z \rangle = 0$$

$$\langle \alpha_x^2 \rangle = \langle \alpha_y^2 \rangle = \langle \alpha_z^2 \rangle = \frac{\alpha^2}{3}$$

The result stated in equation (3) then follows.

We claim:

1. An optical waveguide sensor comprising:

(a) a single mode fiber optic waveguide having a first end and a second end and including a core surrounded by a cladding and having intermediate said first end and said second end a tapered portion which tapers adiabatically inwardly to a waist and then adiabatically outwardly by variation of said cladding whereby under operating conditions the evanescent electromagnetic field associated with the guided mode of said waveguide is externally accessible in the region of said tapered portion;

(b) an optical source optically coupled to said first end of said waveguide; and (c) a detector coupled to said second end of said waveguide for detecting optical radiation modulated or coupled into said waveguide at said tapered portion.

2. A sensor according to claim 1 wherein said tapered portion is in the form of a loop.

3. A sensor according to claim 2 further comprising a mount supporting said loop.

4. A sensor according to claim 3 further comprising a cap for fitting to said mount over said loop.

5. A sensor according to claim 1, wherein said optical source comprises a laser.

6. A sensor according to claim 1, wherein said detector comprises a photodiode.

7. A sensor according to claim 6, further comprising a filter positioned between said optical waveguide and said detector.

8. A sensor according to claim 7 wherein said filter is adapted to filter out optical wavelengths generated at said optical source.

9. A sensor according to claim 1, further comprising means for binding a chemical or biological compound on said tapered portion.

10. A sensor according to claim 9 wherein said means for binding a chemical or biological compound comprises a silane.

\* \* \* \* \*